United States Patent [19]
Engelhardt et al.

[11] Patent Number: 5,473,136
[45] Date of Patent: Dec. 5, 1995

[54] METHOD AND APPARATUS FOR THE MACHINING OF MATERIAL BY MEANS OF A LASER

[75] Inventors: Ralf Engelhardt, Lubeck; Scheu Manfred, Bisterschied, both of Germany

[73] Assignee: Carl Baasel Lasertechnik GmbH, Germany

[21] Appl. No.: 140,113

[22] PCT Filed: Apr. 30, 1992

[86] PCT No.: PCT/EP92/00951

§ 371 Date: Jan. 31, 1994

§ 102(e) Date: Jan. 31, 1994

[87] PCT Pub. No.: WO92/19415

PCT Pub. Date: Nov. 12, 1992

[30] Foreign Application Priority Data

May 3, 1991 [DE] Germany ............... 41 14 492.9

[51] Int. Cl.⁶ .................................................. B23K 26/00
[52] U.S. Cl. ................... 219/121.62; 219/121.83
[58] Field of Search ............ 219/121.62, 121.11, 219/121.6, 121.61, 121.83

[56] References Cited

U.S. PATENT DOCUMENTS

| | | | |
|---|---|---|---|
| 4,504,727 | 3/1985 | Melcher et al. | 219/121.6 |
| 4,682,594 | 7/1987 | Mok | 128/303.1 |
| 4,720,621 | 1/1988 | Langen | 219/121.62 |
| 4,769,523 | 9/1988 | Tanimoto et al. | 219/121.6 |
| 4,939,336 | 7/1990 | Meyer et al. | 219/121.62 |
| 4,960,970 | 10/1990 | Schneiter | 219/121.6 |
| 5,204,517 | 4/1993 | Cates et al. | 219/121.62 |

FOREIGN PATENT DOCUMENTS

| | | |
|---|---|---|
| 195375 | 9/1986 | European Pat. Off. . |
| 312650 | 4/1989 | European Pat. Off. . |
| 3918618 | 12/1990 | Germany . |
| 014797 | 12/1990 | WIPO . |

OTHER PUBLICATIONS

"Optical Studies of Pulsed-laser Fragmentation of Biliary Calculi", Applied Physics B pp. 73–78, 1987.
Laser und Optoelektronik vol. 19, No. 1, Mar. 1987, Stuttgart DE pp. 33–35.
Laser und Optoelektronik vol. 20, No. 4, Aug. 1988, Stuttgart DE pp. 36–39; R. Engelhardt et al.

*Primary Examiner*—Tu Hoang
*Attorney, Agent, or Firm*—Ostrolenk, Faber, Gerb & Soffen

[57] ABSTRACT

In a method for the machining of material using a laser with detection of the material to be machined, laser light is directed at the material via a laser optical system and the light re-emitted by the material is guided to a first detector arrangement which measures the intensity of the light and behind which there is connected an evaluation circuit for controlling the laser power or energy. The energy fed to the material via the laser optical system is measured, and the detector arrangement supplies to the evaluation circuit a display signal which indicates the beginning of the dielectric breakdown. The evaluation circuit reduces the power of the laser and/or interrupts the laser pulse if no display signal has as yet occurred at a predetermined time at which a predetermined energy was fed to the material.

14 Claims, 2 Drawing Sheets

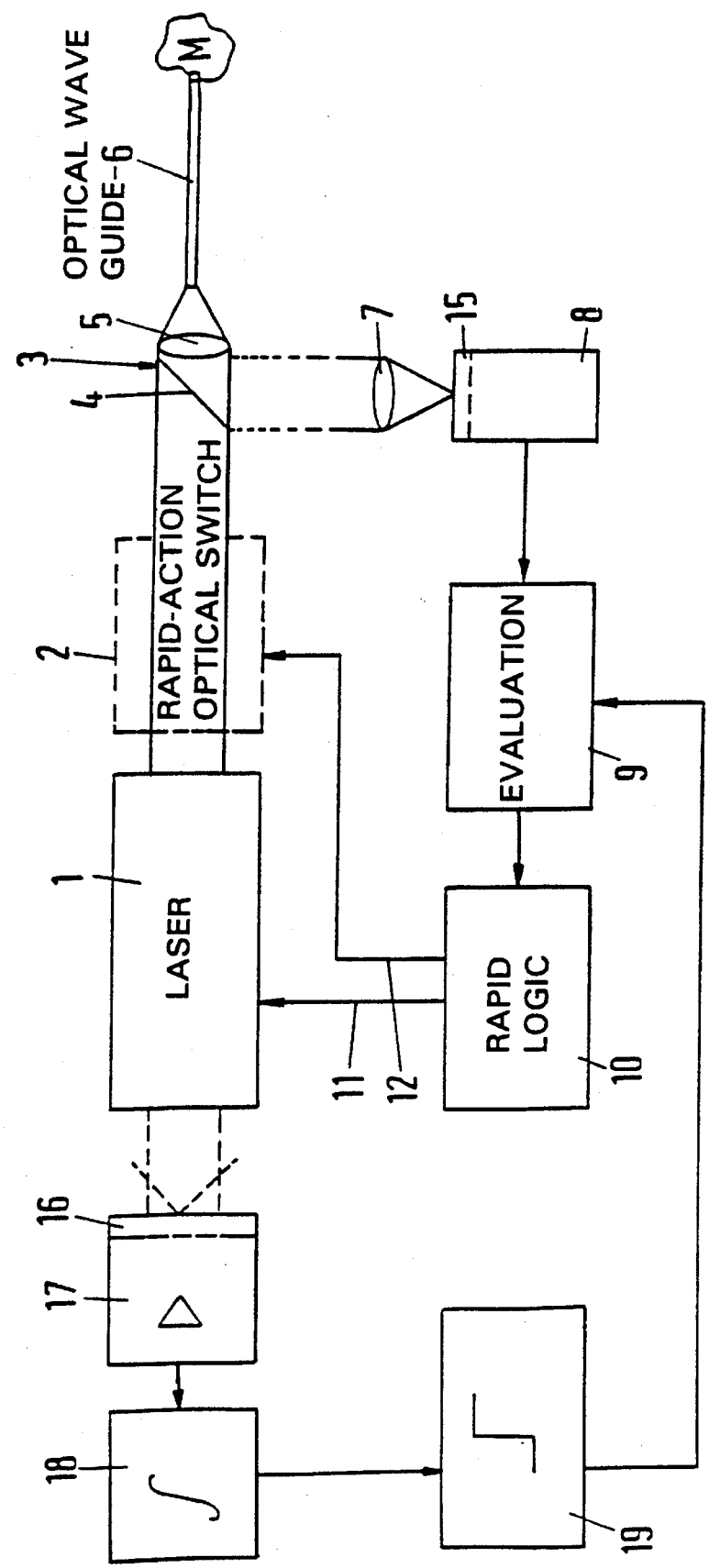

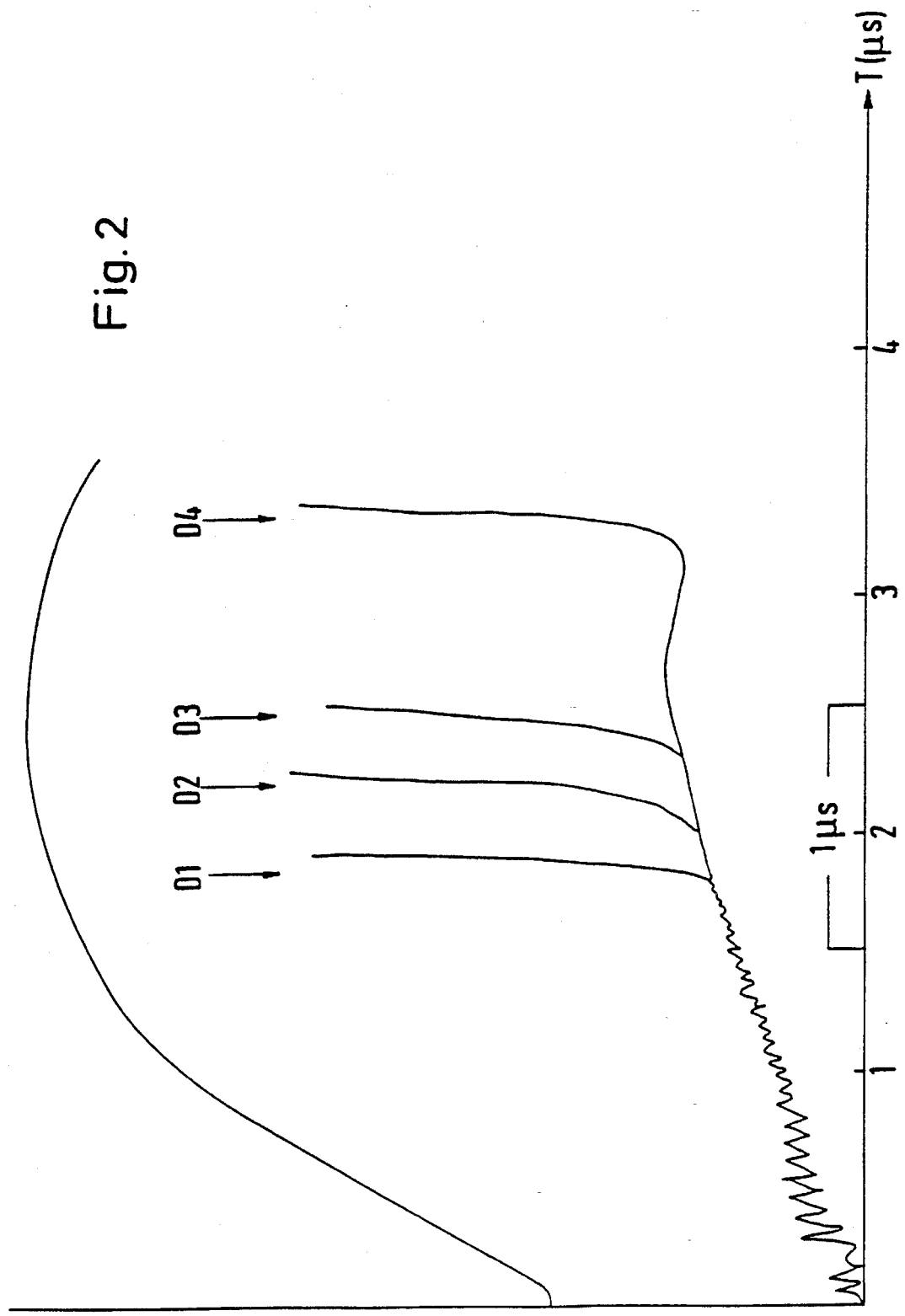

METHOD AND APPARATUS FOR THE MACHINING OF MATERIAL BY MEANS OF A LASER

BACKGROUND OF THE INVENTION

The present invention relates to a method and to an apparatus for the machining of material by means of a laser.

From the literature reference "Optical Studies of Pulsed-Laser Fragmentation of Biliary Calculi", Applied Physics B, Springer Verlag 1987, pages 73 to 78, there is known a method in which the output signal of a laser is directed via a laser optical system, which includes an optical wave guide, at urinary or biliary calculi so as to fragment them. In the laser optical system there is arranged a semi-transparent mirror which guides a part of the light re-emitted, reflected or backscattered by the calculus and guided back via the optical wave guide, to a detector (1) behind which an evaluation circuit in the form of a spectral analyzer is connected.

It is known from EP-A2-01 95 375 to irradiate upon the removal of deposits on tissue the machining area with a low-power pilot laser and to evaluate the re-emitted energy, for instance for three wave lengths, in order to determine whether the material impacted by the pilot laser is formed by a deposit or by tissue which is not to be impacted by a machining laser pulse. For this, however, there is required a separate pilot laser which is used, prior to triggering the machining laser pulse, to determine the material located in front of the laser optical system.

From EP-A1-0 312 650 there is known a method and/or an apparatus of the type indicated above in which only one laser is used, the pulse of which can be interrupted or at least be reduced in its power before reaching full power if it is ascertained, during the rise of the laser pulse by an evaluation of the amplitude characteristic over time of the light returning from the material prior to the dielectric breakdown, that said laser pulse impacts tissue and not material which is to be removed.

DE-A1-39 18 618 describes a similar method and apparatus for the machining of material by means of a laser in which there is measured, in the period between the start of the laser pulse and the earliest possible occurrence of the dielectric breakdown, the intensity of the light re-emitted by the material in at least two predetermined spectral ranges and a quotient of the measured values of the light energy in these predetermined spectral ranges is formed and evaluated and used for the determination of the material impacted by the laser pulse. This method is possible in those cases where corresponding significant differences are present in the spectral characteristic of the light re-emitted by different materials. This, however, is not the case in some applications, for instance in the field of angioplasty. Thus, for instance, normal healthy intima and calcified plaque do not show any significant differences in the fluorescence characteristics upon excitation with a pulsed laser of a wave length of 375 nm and can therefore not be distinguished from each other by this evaluation method, while, for instance, fibrous fatty plaque can be distinguished.

SUMMARY OF THE INVENTION

It is the object of the present invention to create a method and apparatus of the type mentioned above wherein an identification of the material to be machined is possible at slight expense even if the light re-emitted by different materials does not show significant differences in the period of time prior to the dielectric breakdown.

In the method and device of the invention the identification of the composition of the material to be machined is achieved in the manner that the energy which is fed to the material to be machined is measured until the dielectric breakdown caused by the laser pulse commences on the material to be machined.

The result of this measurement can be used for controlling the power of the machining pulses, said power being immediately reduced or the laser pulse being interrupted if, after the feeding of a predetermined energy, no dielectric breakdown has as yet commenced, which indicates that the laser pulse strikes material which is not to be machined.

With a known constant characteristic of the laser pulses, both with respect to the pulse duration and with respect to the power, the energy measurement can, in accordance with a preferred embodiment of the invention, be replaced by a measurement of the time as from the triggering of the laser pulse.

An identifying of the composition of the material to be machined can in this case be achieved in the manner that the period of time is measured which elapses between the triggering of the laser pulse and the commencement of the dielectric breakdown on the material to be machined which is caused by the laser pulse. Due to the simultaneous use of the laser pulse both for the machining and for the identifying of the material, no separate pilot laser is required for the determination of the material.

BRIEF DESCRIPTION OF THE DRAWINGS

The invention will be explained further below with reference to the embodiments shown in the drawing, in which FIG. 1 shows an embodiment of an apparatus for carrying out the method, FIG. 2 shows diagrams which indicate examples for the development over time of the light incident on the detector arrangement.

DESCRIPTION OF PREFERRED EMBODIMENTS

The embodiment shown in FIG. 1 of an apparatus for carrying out the method has a laser 1 the output pulses of which are fed via an optical switch 2 having a high switching rate to a laser optical system 3, the output of which is directed at the material M to be machined via an optical wave guide 6. In the embodiment shown, the laser optical system 3 has, for instance, a beam splitter 4 and a first lens 5 for focusing the laser light pulse on the optical wave guide 6. Light re-emitted by the material M to be machined passes via the optical wave guide 6, the lens 5 and the beam splitter 4 to a further lens 7 which focuses said light via a filter 15 on a detector arrangement 8. The output signal is fed to an evaluation circuit 9 which will be explained further below and which, via logic circuits 10, controls the optical switch 2 via an output line 12. As indicated by an additional output line 11 of the logic circuit 10, the latter can also control the laser 1 itself in which case the optical switch 2 can possibly be dispensed with.

Upon the incidence of a laser pulse of high energy on the material M to be machined, a dielectric breakdown is produced in the immediate vicinity of the material to be machined, said dielectric breakdown triggering a shock wave for machining the material.

This material can, for instance, be a human calculus, for instance a urinary or biliary calculus which is embedded in surrounding tissue. In this case, the shock wave results in a fragmenting of the calculus. The plasma bubble produced results, due to the high temperature of the plasma and the pressure wave produced in this case, in a blasting-off of material, in the removal thereof or in its fragmentation at the target site. However, in this connection care must be taken in many cases and, in particular, in the case of human calculi considered here that the laser pulse emerging at the end of the optical wave guide 6 impacts only the material M to be machined but not the surrounding tissue so that the latter will not be destroyed.

In the case of an angioplasty, this material can be calcified or fibrous fatty plaque which is surrounded by healthy intima of a blood vessel. In this case, the shock wave results in the (desired) removal of plaque. It must, however, be definitely seen to it that the laser pulse emerging at the end of the optical wave guide 6 does not impact the surrounding healthy tissue (intima), since otherwise the wall of the blood vessel can very easily be destroyed and the blood vessel is thus perforated.

For identifying the material impacted by the laser pulse, the energy of the laser pulse fed to the material up to a given time is derived by means of an additional detector 17 which receives a part of the output signal of the laser 1 via a band pass filter 16 for the laser wavelength.

For this purpose, the output signal of the detector 17 is fed, possibly after amplification, to an integrator 18. The integrator 18 can be dispensed with if the detector 17 is an integrating detector.

The output signal of the detector 17 or of the integrator 18 can be fed to a threshold circuit 19 which, after feeding a predetermined energy to the material, supplies an output signal.

The output signal of the threshold value amplifier 19 is fed to the evaluation circuit 9 which furthermore receives the output signal of the detector 8 for the material (sic) returning from the material M, the latter output signal forming a display signal for the start of the dielectric breakdown on the material to be machined.

When the time characteristic of the laser pulse and its maximum power are known and constant, the detector 17 can detect exclusively the triggering of the laser pulse and in the evaluation circuit 9 there is then determined the time difference between the triggering of the laser pulse and the beginning of the dielectric breakdown on the material M since the time elapsed in each case is a measure of the energy fed to the material.

Since for different materials the dielectric breakdown takes place after feeding a specific energy which depends on the material, an identification of the material is possible by measuring the energy fed or the time up to the breakdown. The times or energies in question are in each case typical for a specific machining wave length and the corresponding target material.

The evaluation circuit 9 thus permits very simple and rapid determination as to whether the material to be machined is present at the end of the optical wave guide 6 or whether said end of the optical wave guide is directed at material which must not be impacted by the laser pulse or at least not by a laser pulse of full power.

This type of evaluation will be explained further with reference to FIG. 2.

In FIG. 2, the characteristic of the laser pulse is designated L, while the characteristic of the light re-emitted by different materials M in the form of the output signal of the detector arrangement 8 is designated D1 to D3 for tissue which is strongly calcified to varying degrees, and D4 for tissue which is not calcified or weakly calcified.

In the case of this example, the total energy of a laser pulse was 88 mJ at a wave length of 600 nm and the laser pulse was fed to the material via an optical wave guide having a diameter of 200 micrometers. For other wave lengths and optical wave guides, other values will naturally result, but the principle remains the same.

As can be noted from FIG. 2, the rise in the output signals D1 to D3 of the detector arrangement 8 upon the impinging of the laser light on the calcified tissue, which rise indicates the dielectric breakdown, commences already after about 1.8 to 2.5 microseconds after the triggering of the laser pulse L, which is indicated by the output signal of the detector 17 or the threshold value amplifier 19, while upon impinging on tissue which is not calcified or weakly calcified, this rise takes place only about 3.2 microseconds after the triggering of the laser pulse. These times correspond, in each case, to a predetermined energy fed to the material.

Therefore, if in this case no dielectric breakdown has as yet been indicated by the evaluation circuit after about 2.5 microseconds, this means that the laser pulse impacts material which is not to be machined. The evaluation circuit 9 then reduces, via the line 11, the power of the laser 1 or interrupts the laser pulse via the line 12 and the optical switch 2.

Even if the laser pulse is interrupted at the start of the dielectric breakdown via the line 11 and/or the line 12 by means of the rapid-action optical switch 2, it is still possible to limit the power fed to the material M to a value which is harmless for the material (healthy tissue) which is not to be machined.

We claim:

1. A method for the machining of material by means of a laser with detection of the material to be machined, said method comprising:

directing laser light of a predetermined wavelength and of sufficient energy from said laser via a laser optical system onto said material to cause a dielectric breakdown of said material;

measuring the energy of said laser light directed onto said material via said laser optical system;

guiding light re-emitted by the material to a first detector arrangement;

measuring the intensity of said re-emitted light at said first detector arrangement, said first detector arrangement providing an indication signal if a dielectric breakdown on said material has commenced;

providing said indication signal to an evaluation circuit for controlling the power of said laser light, said evaluation circuit reducing said laser power if no indication signal has as yet occurred after a predetermined energy of said laser light has been directed to said material.

2. A method according to claim 1, wherein said laser is triggered to produce consecutive laser pulses having a constant characteristic; and wherein said measurement of the laser energy directed to said material up to a predetermined time is derived from a measurement of the period of time between the triggering of the laser pulse and the predetermined time.

3. A method according to claim 2, wherein the period of time between the triggering of the laser pulse and the occurrence of said dielectric breakdown is measured and used for determining the material impacted by the laser pulse.

4. A method according to claim 2, wherein the time of the triggering of the laser pulse is measured by an additional detector arrangement which responds to said predetermined wave length of said laser light.

5. A method according to claim 1, wherein for the measurement of the laser energy directed to the material, the power of the laser is measured in an additional detector arrangement, integrated to determine the laser energy resulting therefrom and fed to a threshold detector which, after measuring a predetermined energy, supplies an output signal to the evaluation circuit.

6. A method according to claim 5, wherein an integrating detector is used as the additional detector arrangement.

7. A method according to claim 1, wherein the re-emitted light is conducted to the first detector arrangement via a filter arrangement which masks said predetermined wavelength of said laser light.

8. An apparatus for the machining of material by means of a laser providing laser light pulses of predetermined wavelength and of predetermined power, comprising:

a laser optical system guiding said laser light pulses to said material and deflecting light re-emitted by said material to a first detector arrangement which measures the intensity of said re-emitted light and provides an output signal to an evaluation circuit;

an additional detector arrangement for measuring the energy of said laser light pulses fed to said material via the laser optical system, an output signal of said additional detector arrangement representing said energy being fed to the evaluation circuit;

said first detector arrangement supplying to said evaluation circuit an indication signal indicating a dielectric breakdown of the material; and said evaluation circuit, upon the absence of said indication signal and after measurement of a predetermined energy, doing one of (a) reducing the power of said laser pulses, (b) interrupting said laser pulse via a rapid-action optical switch and (c) reducing the power of said laser pulses and interrupting said laser pulse via a rapid-action optical switch.

9. An apparatus according to claim 8, wherein said additional detector arrangement determines the time of triggering of a laser light pulse and wherein said evaluation circuit measures the time difference between the occurrence of said output signal of said additional detector arrangement and said indication signal of said first detector arrangement indicates said dielectric breakdown of the material and controls one of said laser, said rapid-action optical switch and said laser and said rapid action optical switch.

10. An apparatus according to claim 8, wherein said laser optical system includes a beam splitter which deflects to said first detector arrangement the light re-emitted by said material which is impacted by said laser pulse.

11. An apparatus according to claim 10, wherein said laser optical system comprises a filter arrangement which masks said predetermined wavelength of said laser light and is arranged between said beam splitter and said first detector arrangement.

12. An apparatus according to claim 8, wherein said additional detector arrangement responds exclusively to said predetermined wave length of said laser light.

13. An apparatus according to claim 8, wherein said additional detector arrangement comprises a threshold value amplifier which conducts said output signal to said evaluation circuit.

14. An apparatus according to claim 12, wherein said additional detector arrangement comprises an integrating detector.

* * * * *